United States Patent
Fano

(10) Patent No.: US 8,725,524 B2
(45) Date of Patent: May 13, 2014

(54) FRAUD DETECTION METHOD AND SYSTEM

(75) Inventor: Andrew E. Fano, Lincolnshire, IL (US)

(73) Assignee: Accenture Global Services Limited, Dublin (IE)

(*) Notice: Subject to any disclaimer, the term of this patent is extended or adjusted under 35 U.S.C. 154(b) by 3072 days.

(21) Appl. No.: 10/639,978

(22) Filed: Aug. 13, 2003

(65) Prior Publication Data

US 2005/0044357 A1  Feb. 24, 2005

(51) Int. Cl.
*G06Q 50/22* (2012.01)
*G06Q 50/24* (2012.01)

(52) U.S. Cl.
CPC ............ *G06Q 50/22* (2013.01); *G06Q 50/24* (2013.01)
USPC .................................. 705/2; 705/3

(58) Field of Classification Search
CPC ................... G06Q 50/22; G06Q 50/24
See application file for complete search history.

(56) References Cited

U.S. PATENT DOCUMENTS 5,253,164 A * 10/1993 Holloway et al. ............ 705/2

OTHER PUBLICATIONS

Educators Mutual Insurance Association, BeneFacts, "Watch for Improved Explanation of Benefits", Mar. 2002, p. 1.*
"Application of Genetic Algorith and k-Nearest Neighbour Method in Medical Fraud Detection" by Xin Yao, Hongxing He, and Warwick Greco, X. Yao et al. (Eds.): SEAL '98, LNCS 1585, pp. 74-81, 1999.*

* cited by examiner

*Primary Examiner* — Eliza Lam
(74) *Attorney, Agent, or Firm* — Harrity & Harrity, LLP

(57) ABSTRACT

A method for determining the legitimacy of an insurance claim includes the steps of receiving codes that identify a service for which payment is requested from an insurance provider. Services that might have been upcoded or miscoded to the claimed service are also identified. An insured, a patient or a family member or care giver can be queried about the occurrence of observable aspects of the service that is billed as well as a service that might have been upcoded to what is billed. Responses to the queries suggest the legitimacy or illegitimacy of the claim.

20 Claims, 2 Drawing Sheets

FRAUD DETECTION METHOD AND SYSTEM

BACKGROUND OF THE INVENTION

Insurance fraud is costly to insurance providers and ultimately to their customers. A common form of insurance fraud occurs when services that were actually provided are represented to the insurance company as something more, or the services that were rendered are "upcoded" to more expensive and/or elaborate goods and services. In an attempt to combat insurance fraud, some insurers provide their policy holders with a statement of benefits (i.e., a statement of the payments) that were provided to a third-party service provider under an insurance policy. These benefit statements are also known as an "explanation of benefits" or an "EOB." Insurers frequently ask their insureds (i.e., their insured customers) to verify that services listed on an EOB were actually rendered.

At least one problem with combating insurance fraud using an EOB is that many services and especially medical procedures, are not understood by a lay person. Asking a lay person to confirm his or her receipt of a medical procedure described in technical jargon on an EOB is problematic. At least with regard to health-care, insured persons frequently have no understanding of services they were provided or billed for and are therefore unable to confirm the contents of a billing statement from a medical service provider. In instances where services are provided without the insured's understanding of them makes it difficult for an insurance provider to determine whether or not a claim made by service providers is legitimate. A method and system by which a fraudulent claim can be more accurately identified would be an improvement over the prior art.

DETAILED DESCRIPTION OF A PREFERRED EMBODIMENT

A method of determining the legitimacy of an insurance claim includes steps of first identifying when a claim is made by an insured person or on behalf of an insured person. After a claim is identified, the occurrence of objective and layperson-identifiable events or conditions (i.e., those that are readily observable and identifiable by the insured, and which require no specialized training or understanding but which tend to confirm that the insured service or goods were provided) are established directly from the insured by posing questions to the insured that are designed to produce responses that will suggest or confirm the legitimacy or illegitimacy of an insurance claim. The questions are designed to indirectly query whether the service provider actually rendered a billed service and/or whether those services were warranted. By posing questions to an insured regarding events and/or conditions that tend to confirm or deny the legitimacy of a claim, an insurance provider can identify potentially fraudulent claims.

Figure 1:
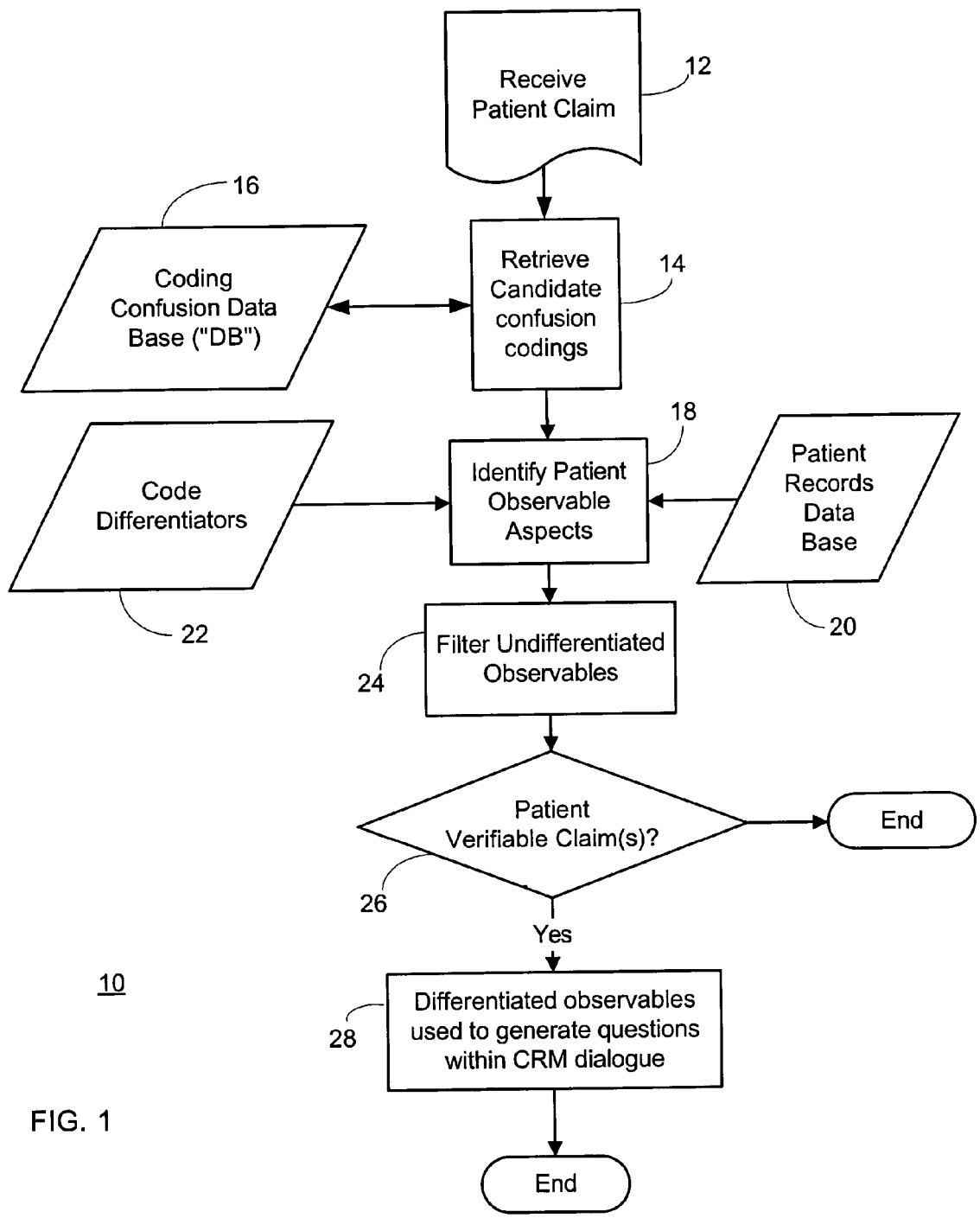
FIG. 1 is a flow chart depiction of a method for detecting fraud in an insurance claim.

FIG. 1 depicts steps of a method 10 of determining the legitimacy of an insurance claim. The method depicted in FIG. 1 is with respect to a medical insurance claim, however the method can be readily used to determine the legitimacy of other insurance claims. As used herein, a "claim" and an "insurance claim" are both considered to be any request for payment or re-imbursement for losses and/or expenses incurred by an insured. An "insured" is a person who is entitled to receive insurance benefits under an insurance contract (i.e., an insurance "policy") with an insurance provider. An "insurance provider" is usually a state regulated company engaged in the business of providing insurance.

Examples of "claims" include bills sent to an insurance company for reimbursement of the cost to repair and/or reconstruct a vehicle after a collision or theft. Claims also include bills sent to an insurance provider by a medical service provider for payment of the cost to render medical services or therapeutic goods to the insured. Upon receipt of a claim, an insurance provider pays either the insured person or pays a third-party goods/service provider. For simplicity, the steps depicted in FIG. 1 are with respect to a claim made to an insurance provider under a medical insurance policy.

As is well-known in the medical insurance industry, after a medical service is provided to an insured, the cost of the service that was rendered to the insured is often billed in whole or in part directly to an insurance provider. Typically it is difficult for the insurance providers to economically verify the need for the claimed services, and that the claimed services were rendered.

When medical services are billed, they are usually identified to the insurance provider using numeric codes, each of which identifies a service that was ostensibly rendered. It is also known that many insurance companies reimburse service providers for various services at fixed fees. For example, simple pneumonia can be paid at one rate whereas complex pneumonia is paid at a higher rate. A routine visit to see a physician is usually paid at one amount whereas an office visit and inoculations is usually paid at a higher amount. When billing an insurance company for services that were rendered, a service provider must determine the code that most accurately identifies the service or procedure that was rendered to the insured. When multiple services are rendered to an insured, the service provider identifies each service with its own corresponding code so that each service that was rendered will be paid for, at least according to the coverage to which the insured is entitled.

A service or procedure that was rendered is sometimes "upcoded" either because of error or intent. Upcoding a service means that the insurance provider will be billed for a more costly service and a larger payment will be made to the service provider by the insurance provider. Simple pneumonia, for example, is often "upcoded" to complex pneumonia, and as a frequent diagnosis this confusion can lead to massive overpayments to providers by insurance companies.

For every medical service or medical procedure actually provided to an insured, there is a non-zero probability that the rendered procedure will be incorrectly coded prior to submission of the claim to an insurance provider. Incorrectly coded procedures often occur because of mistakes, such as confusion as to the scope or meaning of a code or a typographical error. On the other hand, incorrectly coded procedures can also occur deliberately, i.e., because of fraud or abuse An objective of the method disclosed and claimed herein is to identify which claims might be erroneous by way of extrinsic, patient-observable events, the occurrence or non-occurrence of which suggest that a claim is correctly coded or might be incorrectly coded.

In FIG. 1, step 12, a request for payment for goods or services that were provided to an insured, is received by an insurance company, usually in the form of a bill from a service provider. In alternative embodiments, the claim is in the form of a receipt or other documents that show that the insured incurred a loss and is seeking reimbursement. Whether the claim received in step 12 is in writing; an electronic form, an e-mail message, or via an oral communication is not critical. Whether the claim is received from the service provider or from the insured is also not critical. In step 12, an insurance provider receives a claim or a demand for payment for a service rendered to an insured (i.e., a person to whom insurance coverage is provided) or for goods that were provided to an insured.

For each code received in step 12, (each of which identifies a service that was ostensibly rendered to an insured) in step 14 the codes for services that are potentially confused with, or upcoded from, to the billed-for code, are retrieved from a coding confusion database, "DB" 16. Using the aforementioned pneumonia example, when the billed code of step 12 is for simple pneumonia, in step 14, the code for a simple pneumonia will be retrieved from the confusion database 16.

The coding confusion database DB 16 is built using mathematical probabilities of miscoding or upcoding a specific service that was rendered to a patient based on the patient's personal data and/or demographic data (i.e. age, gender, race/ethnicity, tests ordered, test results, medical history, etc.) and is compiled using historical data on medical claims. The database is stored in a computer-readable media such as a magnetic disk, a CD-ROM or a magnetic tape, all of which are well-known in the computer art.

Stated alternatively, for each claim that was received in step 12, in step 14, a list of codes of services is created that are statistically likely to have been confused with, or upcoded to be the service ostensibly identified on the claim of step 12. Inasmuch as a code that represents a rendered service is subject to confusion or mistake, step 14 will create a list of codes that are statistically confused with the actual service that was rendered.

As is well known, some aspects of a medical procedure or service are observable by a patient. For example, whether a patient saw a particular service provider is certainly observable by a patient. Whether a patient underwent a surgical procedure is also observable by a patient. Whether a patient has been prescribed a drug therapy or is following a drug treatment regimen is also observable by a patient. In step 18, patient-observable aspects of the coded service of the claim are retrieved from a database of code differentiators 22. In addition, in step 18, patient-observable aspects of the codes generated in step 14 are also retrieved from the database of code differentiators 22. Patient data records are also retrieved from a patient records database 20.

The database of code differentiators 22 is a library of aspects of a coded service that are observable by a patient. A patient's confirmation of the occurrence of a differentiator at least suggest that a particular service was rendered.

Patient-observable aspects of a coded service and of a possibly miscoded service may include (but are not limited to): the identity of the service providers used, the number of meetings with the service provider, the duration of the meetings, the services rendered, tools and materials used, the topics discussed including diagnoses and treatments (or more generally, approaches to problems), aspects of the problem (e.g. symptoms), etc. The patient-observable aspects are used as determinators of the legitimacy of a claim for which insurance coverage is sought.

As is well-known, patient-observable aspects can vary from patient to patient. Accordingly, in step 14, patient data retrieved from a patient records data base 20 is used to identify patient-observable aspects of a procedure that was ostensibly rendered as well as a procedure that might have been upcoded or which might have been confused with the procedure that was billed.

In step 14, each coded service and each possibly miscoded/upcoded service are considered to be a coding pair. For each coding pair having patient observable aspects, a determination is made in step 24 whether the patient observable aspects of a coded service and the patient observable aspects of the possible miscoded service are differentiated. Undifferentiated aspects of both services are filtered, i.e., not considered to be of value in identifying miscoding. In other words, the undifferentiated patient observables of a coding pair are ignored from further consideration as useful in determining the legitimacy of a claim. In step 24, if patient observable aspects of the coded service and a possibly miscoded service are differentiated by more than a minimum threshold, each such patient observable aspect is useful in determining, from a patient, whether a claim is legitimate. Stated alternatively, if a patient-observable aspect for a coding pair is indistinguishable, such a patient-observable aspect will be of no value in verifying the occurrence of either service.

The result of the filtration step 24 is preferably one or more patient-observable aspects of a coding pair, the existence or non-existence of which suggests either the service that was properly coded in the claim or a possibly miscoded. For example, the determination of some event or condition "x" by the patient confirms that the service that was coded in the claim could not have been rendered. Or, the determination of an event or condition "Y" by the patient confirms that another service that was not coded must have been the service that was rendered.

In step 26, a determination is made whether a miscoding could be substantiated by patient observable aspects of either portion of a coding pair. A determination is made whether there are enough patient observable aspects of a coding pair that a lucid and alert patient is likely to be able to provide discriminating information that will suggest a miscoding with enough probability to conduct further investigation? Are the patient observable aspects sufficiently numerous that verified, suggest a miscoding with enough probability to conduct further investigation?

If the decision of step 26 is negative, i.e., there are either no patient observable aspects by which a claim's legitimacy can be validated via the insured, the legitimacy of a claim cannot be determined by the insured and the process depicted in FIG. 3 terminates. If the decision of step 26 is affirmative, there are patient observable aspects that can be used to determine the legitimacy of a claim whereupon step 28 is performed wherein patient observable aspects of a coding pair are used by an insurance provider for inclusion within a dialogue with the patient.

While it is certainly possible to ask an insured person a direct question whether a claim of a service provider is legitimate, as set forth above, lay persons are usually unable to state whether a particular procedure or service was performed. In addition, insurance providers might not want to suggest that a service provider's claim is improper. Therefore, the preferred embodiment of the invention contemplates a dialogue between an insured person and a representative of an insurance provider (e.g., a sales agent, claims adjuster etc.) by which questions can be posed to an insured under the rubric of a customer satisfaction survey, i.e., a customer relationship management (CRM) function. Superficially benign questions, i.e., superficially unrelated to determining the legitimacy of an insurance claim, are posed to the insured, responses to which can suggest whether a claim is legitimate. By conducting a dialogue with an insured, investigative questions can be followed up with additional pertinent questions as needed.

The preferred dialogue with an insured is embodied as a series of questions that elicit the insured's confirmation of the occurrence of patient observable aspects of at least one code of a coding pair. Stated alternatively, the preferred dialogue confirms the occurrence of a patient-observable aspect of the service that was billed or, another service that is statistically likely to be confused with the service that was billed.

A claim investigation dialogue with an insured is preferably conducted as a CRM dialogue in which an insured is asked for feedback about the quality of the services they received. In one embodiment, a claim investigation dialogue occurs in person, between an insured and a representative of an insurance provider. In a second embodiment, such a dialogue takes place via a telephone conference. In another embodiment, a claim investigation dialogue can occur "online" which means via one or more e-mail messages exchanged between an insured and a representative of an insurance company; by way of a "chat room" or by way of a web-site from which strings of text can be read and entered. Questioning an insured ostensibly to determine his or satisfaction as opposed to whether a service was or was not rendered reduces the likelihood that an insured will misrepresent or color his or her recollection of patient observable aspects. A CRM dialogue about the insured's satisfaction with the services ostensibly rendered can identify whether services that were billed were actually rendered.

Within a broader dialogue with an insured in which the insured's satisfaction with the services they received is queried, patient observable aspects can be verified by posing questions to an insured such as "When did you first notice [a symptom or symptoms of a malady for which treatment was ostensibly rendered]? To which there are two likely responses: a) a date certain or a time frame when the symptom or symptoms were first noticed; b) that the insured never experienced the symptom or symptoms.

An affirmation in the response to the foregoing question that a symptom was experienced tends to confirm the legitimacy of a claim for medical treatment for any malady that causes the complained-of symptom. On the other hand, an insured's denial that he or she ever experienced symptoms of the malady for which treatment was allegedly rendered suggests that the claim for payment or reimbursement might have been miscoded.

Another question to an insured that determines when a symptom of a malady was first experienced, or a follow-up question on the occurrence of symptoms can also be useful to determine the legitimacy of a claim. A question such as "When did you first notice [the complained-of symptom]?" will usually elicit one of two responses: a) a date on which a symptom was experienced; b) the insured never experienced the symptom.

The insured identification of a date or an identifiable date on which a symptom was experienced, tends to legitimize a claim for payment or reimbursement for treatment for the complained-of symptom. On the other hand, a denial that a symptom of a malady for which treatment was allegedly rendered tends to show that the claim for payment or reimbursement might have been miscoded or fraudulent.

Questions directed to a service provider's cure, treatment or other resolution, are also useful to determine the legitimacy of a claim. A question such as: "Did your [problem; symptom; complaint] get resolved to your satisfaction?" will usually elicit one of four responses: a) Yes, with or without additional comments; b) No with or without additional comments; and c) that the insured was never diagnosed with "x" condition or malady; or d) that the insured never experienced the problem or symptom. A denial that the insured was ever diagnosed with the ostensibly treated malady or an indication that the insured never experienced associated symptoms tends to show that a claim for insurance treating the malady might have been miscoded or fraudulent.

In addition to the foregoing, questions addressed to the service provider's identity can help determine whether a claim for insurance payment or re-imbursement is legitimate. In some instances, it might be appropriate to use pictures, photographs or other media to refresh the memory of the insured. A question such as: "Did you find Dr. X to be warm and/or careful?" might elicit several responses. A response that the insured either liked Dr. X or disliked Dr. X tends to show that Dr. X at least met the insured. On the other hand, a denial by a lucid insured person that he or she ever met Dr. X can indicate miscoding or fraud.

Questions about the patient's satisfaction with the provider for a specific number of meetings can also be useful in detecting miscoding or fraud. For instance, a dialogue such as: "Dr. X monitored your care throughout your stay. We understand she visited you at least 6 times. Overall are you satisfied with her care?" can elicit a variety of responses. A denial that the insured ever met Dr. X or a denial that the insured saw Dr. X "at least 6 times" can indicate that a claim was miscoded or that the claim is fraudulent.

Questions that ascertain whether the service provider explained a procedure or why a procedure was required or performed are useful in detecting miscoding and possible fraud. For instance, a question such as: "Did the doctor explain why the [billed for and described in layman's terms] procedure was necessary?" could have at least three responses. An affirmative and a negative response might be of little value, however, a response wherein the insured states that he or she does not recall ever receiving the billed-for procedure might indicate a miscoding or possible fraud.

Questions that ascertain whether the service provider explained the risks of a procedure can also indicate a miscoding or possible fraud. A question such as: "Did the doctor explain the possible side effects of [the billed for procedure in layman's terms] with you beforehand?" can also be useful in identifying miscoding or fraud. An answer from the insured that he or she does not recall receiving the billed for procedure might indicate miscoding or possible fraud. Still other questions, such as an explanation of the tools, drugs or treatment, and whether the insured was satisfied with a treatment or service can be useful as well.

In the foregoing description, the services rendered to an insured were medical services and a patient is queried about "patient observable aspects." In some instances, wherein the patient is an infant, a minor, incapacitated or not lucid, the term "patient observable aspect" should be construed to include aspects of a service that are observable by the insured parent of a minor, a member of an incapacitated patient's family or a caregiver of an incapacitated patient. In a more general application of the method, the aforementioned "patient-observable aspects" of a billed service are "insured-observable aspects" in that an insured person is queried about the occurrence of observable events.

Which question or questions are used will depend on the type of procedure billed. For example, whether an explanation of a procedure by a service provider is typically necessary; whether there are particular or significant risks that need to be discussed; whether tools that need explanation are necessary, or whether the insured experience for a procedure varies enough to warrant asking about satisfaction.

Figure 2:
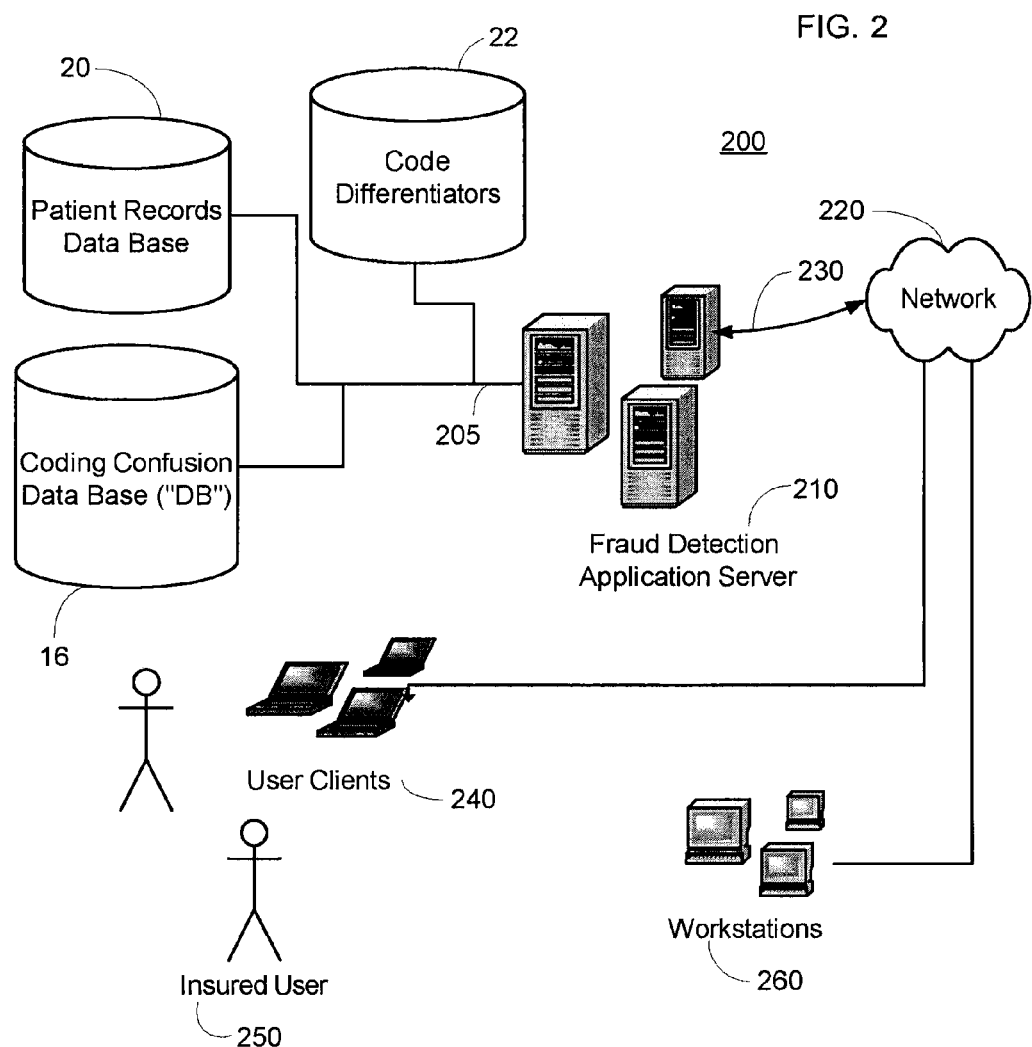
FIG. 2 is a depiction of a system for detecting fraud in an insurance claim.

FIG. 2 is a depiction of a system 200 for detecting fraud in an insurance claim and provides the functionality by which a claim investigation dialogue can occur "on-line." As is well known, a "computer" is comprised of a processor that executes program instructions that are stored in memory to which the processor is coupled. At least part of the system 200 of FIG. 2, is one or more computers or "servers" 210 that execute program instructions stored in either local memory (e.g., random access memory or RAM, not shown) or in a mass storage device and which imbue the server 210 with the functionality described above and depicted by the steps shown in FIG. 1. As such, the server 210 performs steps of the method shown in FIG. 1.

In the system of FIG. 2, one or more mass storage devices such as magnetic hard disk drives, CR-ROM drives or magnetic tape drives, store the coding confusion database 16, the patient records database 20 and the code differentiators database 22. The one or more mass storage devices that store the databases are coupled to the fraud detection application server 210 via a bus 205 that couples the mass storage devices to the actual processors of the sever 210 (not shown but well known in the art) that execute stored program instructions and which operate on stored data. Busses 205 that couple storage devices to processors are well-known in the art.

Program instructions stored in the server 210 cause it to receive claims from service providers encoded to identify goods or services for which payment is requested, preferably by receiving data via the network 220 to which service providers (not shown) are also coupled. Codes for services that might have been upcoded and/or which are confused with each other are retrieved from the coding confusion database as set forth above. Patient records and code differentiators are also retrieved as set forth above.

As set forth above, one way to conduct a dialogue with an insured is by e-mail messages exchanged between an insured user 250 and a representative of an insurance company. In FIG. 2, a representative of an insurance provider communicates via e-mail using a workstation 260. E-mail messages from the workstation 260 are routed to the through the fraud detection application server 210 and to the insured user client computer 240 via a data network 220. Inasmuch as an electronic exchange with an insured is enabled or recorded by the server 210, it is considered as performing the function of querying the insured about the occurrence of observable aspects.

In another embodiment that provides a more interactive exchange, a dialogue can be had by way of a "chat room" hosted by the fraud detection application server 210. In yet another embodiment, the server 210 hosts a web-site into which strings of text can be input into fields or dialogue windows and from which they can be read.

From the foregoing, it should be apparent that insurance fraud and abuse can be reduced by querying an insured person about unambiguous, insured-observable aspects of goods provided to an insured or services rendered to an insured and for which reimbursement is sought from an insurance provider. Instead of sending cryptic benefits statements to an insured with a request to identify fraudulent claims, as in the prior art, the method disclosed and claimed herein accumulates evidence of improper claims through statements of an insured person. When used to detect improper claims for goods, such as materials provided to a homeowner or car owner, the questions posed to an insured need to elicit responses that confirm or deny that the goods for which reimbursement is sought were actually provided.

What is claimed is:

1. A method comprising:
receiving, by a computer, a first code that identifies a first service for which payment is requested from an insurance provider;
identifying, by the computer, at least one second code that represents a second service that is statistically likely to have been confused with the first service;
identifying, by the computer, at least one first insured observable aspect of the first service,
the at least one first insured observable aspect comprising at least one of an event or condition that would have been experienced during a provision of the first service;
identifying, by the computer, at least one second insured observable aspect of the second service,
the at least one second insured observable aspect comprising at least one of an event or condition that would have been experienced during a provision of the second service;
filtering, by the computer and based on a differentiation of the at least one first insured observable aspect and the at least one second insured observable aspect, to determine whether a differentiated first insured observable aspect and a differentiated second insured observable aspect are available;
determining, by the computer, that the differentiated first insured observable aspect and the differentiated second insured observable aspect are available;
determining, by the computer and based on the determining that the differentiated first insured observable aspect and the differentiated second insured observable aspect are available, whether information associated with the differentiated first insured observable aspect and the differentiated second insured observable aspect is sufficient to determine if a claim associated with the first service is valid; and
initiating, by the computer and based on determining that the information associated with the differentiated first insured observable aspect and the differentiated second insured observable aspect is sufficient to determine if the claim associated with the first service is valid, a communication session with a person associated with the provision of the first service about an occurrence of at least one of the differentiated first insured observable aspect or the differentiated second insured observable aspect.

2. The method of claim 1 further comprising:
authenticating the first code based on a response received from the person.

3. The method of claim 1, where initiating the communication session further comprises:
initiating, by the computer, a dialogue between the person and a representative of the insurance provider.

4. A method comprising:
receiving, by a computer, a first code that identifies first goods for which payment is requested from an insurance provider;
identifying, by the computer, at least one second code that represents second goods that are statistically likely to have been confused with the first goods;
identifying, by the computer, at least one first observable aspect of the first goods,
the at least one first observable aspect comprising at least one of an event or condition that would have been experienced during a provision of the first goods;
identifying, by the computer, at least one second observable aspect of the second goods,
the at least one second observable aspect comprising at least one of an event or condition that would have been experienced during a provision of the second goods;

filtering, by the computer and based on a differentiation of the at least one first insured observable aspect and the at least one second insured observable aspect, to determine whether a differentiated first insured observable aspect and a differentiated second insured observable aspect are available;

determining, by the computer, that the differentiated first insured observable aspect and the differentiated second insured observable aspect are available;

determining, by the computer and based on the determining that the differentiated first insured observable aspect and the differentiated second insured observable aspect are available, whether information associated with the differentiated first insured observable aspect and the differentiated second insured observable aspect is sufficient to determine if a claim associated with the first goods is valid; and initiating, by the computer and based on determining that the information associated with the differentiated first insured observable aspect and the differentiated second insured observable aspect is sufficient to determine if the claim associated with the first service is valid, a communication session with a person associated with the provision of the first goods about an occurrence of at least one of the differentiated first insured observable aspect or the differentiated second insured observable aspect.

5. The method of claim 4 further comprising:
authenticating the first code based on a response received from the person.

6. The method of claim 4, where initiating the communication session further comprises:
initiating, by the computer, a dialogue between the person and a representative of the insurance provider.

7. An apparatus comprising:
a processor;
a memory storing program instructions which cause the processor to:
receive a first code that identifies a first service for which payment is requested from an insurance provider;
identify at least one second code that represents a second service that is statistically likely to have been confused with the first service;
identify at least one first insured observable aspect of the first service,
the at least one first insured observable aspect comprising at least one of an event or condition that would have been experienced during a provision of the first service;
identify at least one second insured observable aspect of the second service,
the at least one second insured observable aspect comprising at least one of an event or condition that would have been experienced during provision of the second service;
filter, based on a differentiation of the at least one first insured observable aspect and the at least one second insured observable aspect, to determine whether a differentiated first insured observable aspect and a differentiated second insured observable aspect are available;
determine that the differentiated first insured observable aspect and the differentiated second insured observable aspect are available;
determine, based on the determining that the differentiated first insured observable aspect and the differentiated second insured observable aspect are available, whether information associated with the differentiated first insured observable aspect and the differentiated second insured observable aspect is sufficient to determine if a claim associated with the first service is valid; and
initiate, based on determining that the information associated with the differentiated first insured observable aspect and the differentiated second insured observable aspect is sufficient to determine if the claim associated with the first service is valid, a communication session with a person associated with the provision of the first service about an occurrence of at least one of the differentiated first insured observable aspect or the differentiated second insured observable aspect.

8. The apparatus of claim 7, where the processor is further to:
authenticate the first code based on a response received from the person.

9. The apparatus of claim 7, where processor is further to:
initiate, while initiating the communication session, a dialogue between the person and a representative of the insurance provider.

10. An apparatus comprising:
a processor;
a memory storing program instructions which cause the processor to:
receive a first code that identifies first goods for which payment is requested from an insurance provider;
identify at least one second code that represents second goods that is statistically likely to have been confused with the first goods;
identify at least one first insured observable aspect of the first goods,
the at least one first insured observable aspect comprising at least one of an event or condition that would have been experienced during a provision of the first goods;
identify at least one second insured observable aspect of the second goods,
the at least one second insured observable aspect comprising at least one of an event or condition that would have been experienced during a provision of the second goods;
filter, based on a differentiation of the at least one first insured observable aspect and the at least one second insured observable aspect, to determine whether a differentiated first insured observable aspect and a differentiated second insured observable aspect are available;
determine that the differentiated first insured observable aspect and the differentiated second insured observable aspect are available;
determine, based on the determining that the differentiated first insured observable aspect and the differentiated second insured observable aspect are available, whether information associated with the differentiated first insured observable aspect and the differentiated second insured observable aspect is sufficient to determine if a claim associated with the first goods is valid; and
initiate, based on determining that the information associated with the differentiated first insured observable aspect and the differentiated second insured observable aspect is sufficient to determine if the claim associated with the first service is valid, a communication session with a person associated with the provision of the first goods about an occurrence of at least one of the differentiated first insured observable aspect or the differentiated second insured observable aspect.

11. The apparatus of claim 10, where the processor is further to:
    authenticate the first code based on a response received from the person.

12. The apparatus of claim 10, where the processor is further to:
    initiate, while initiating the communication session, a dialogue between the person and a representative of the insurance provider.

13. The method of claim 1, where at least one of the at least one first insured observable aspect or the at least one second insured observable aspect comprises one or more of:
    an identify of a service provider,
    a number of meetings with the service provider,
    a duration of a meeting with the service provider,
    tools and materials used by the service provider,
    symptoms discussed with the service provider, or
    diagnoses and treatments discussed with the service provider.

14. The apparatus of claim 7, where at least one of the at least one first insured observable aspect or the at least one second insured observable aspect comprises one or more of:
    an identify of a service provider,
    a number of meetings with the service provider,
    a duration of a meeting with the service provider,
    tools and materials used by the service provider,
    symptoms discussed with the service provider, or
    diagnoses and treatments discussed with the service provider.

15. The method of claim 4, where at least one of the at least one first insured observable aspect or the at least one second insured observable aspect comprises one or more of:
    an identify of a service provider,
    a number of meetings with the service provider,
    a duration of a meeting with the service provider,
    tools and materials used by the service provider,
    symptoms discussed with the service provider, or
    diagnoses and treatments discussed with the service provider.

16. The apparatus of claim 10, where at least one of the at least one first insured observable aspect or the at least one second insured observable aspect comprises one or more of:
    an identify of a service provider,
    a number of meetings with the service provider,
    a duration of a meeting with the service provider,
    tools and materials used by the service provider,
    symptoms discussed with the service provider, or
    diagnoses and treatments discussed with the service provider.

17. The method of claim 3, further comprising:
    providing, during the initiated dialogue and from the representative, one or more questions regarding at least one of:
      the at least one first insured observable aspect, or
      the at least one second insured observable aspect; and
    receiving, based on the one or more questions, information from the person.

18. The method of claim 6, further comprising:
    providing, during the initiated dialogue and from the representative, one or more questions regarding at least one of:
      the at least one first insured observable aspect, or
      the at least one second insured observable aspect; and
    receiving, based on the one or more questions, information from the person.

19. The apparatus of claim 9, where the processor is further to:
    provide, during the initiated dialogue and from the representative, one or more questions regarding at least one of:
      the at least one first insured observable aspect, or
      the at least one second insured observable aspect; and
    receive, based on the one or more questions, information from the person.

20. The apparatus of claim 12, where the processor is further to:
    provide, during the initiated dialogue and from the representative, one or more questions regarding at least one of:
      the at least one first insured observable aspect, or
      the at least one second insured observable aspect; and
    receive, based on the one or more questions, information from the person.

* * * * *